US00PP28561P2

(12) United States Plant Patent
Danziger

(10) Patent No.: US PP28,561 P2
(45) Date of Patent: Oct. 24, 2017

(54) **NEW GUINEA *IMPATIENS* PLANT NAMED 'DHARWHITE'**

(50) Latin Name: *Impatiens hawkeri*
Varietal Denomination: DHARWHITE

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 5 days.

(21) Appl. No.: 14/999,081

(22) Filed: Mar. 28, 2016

(51) Int. Cl.
*A01H 5/02* (2006.01)

(52) U.S. Cl.
USPC ..... Plt./318.2

(58) Field of Classification Search
USPC ..... Plt./317, 318.1, 318.2
See application file for complete search history.

*Primary Examiner* — Susan McCormick Ewoldt
(74) *Attorney, Agent, or Firm* — Cassandra Bright

(57) ABSTRACT

A new and distinct *Impatiens* cultivar named 'DHARWHITE' is disclosed, characterized by large white flowers, well branched plant form and good sun resistance. The new variety is an *Impatiens*, normally produced as an outdoor garden or container plant.

2 Drawing Sheets

Figure 1:
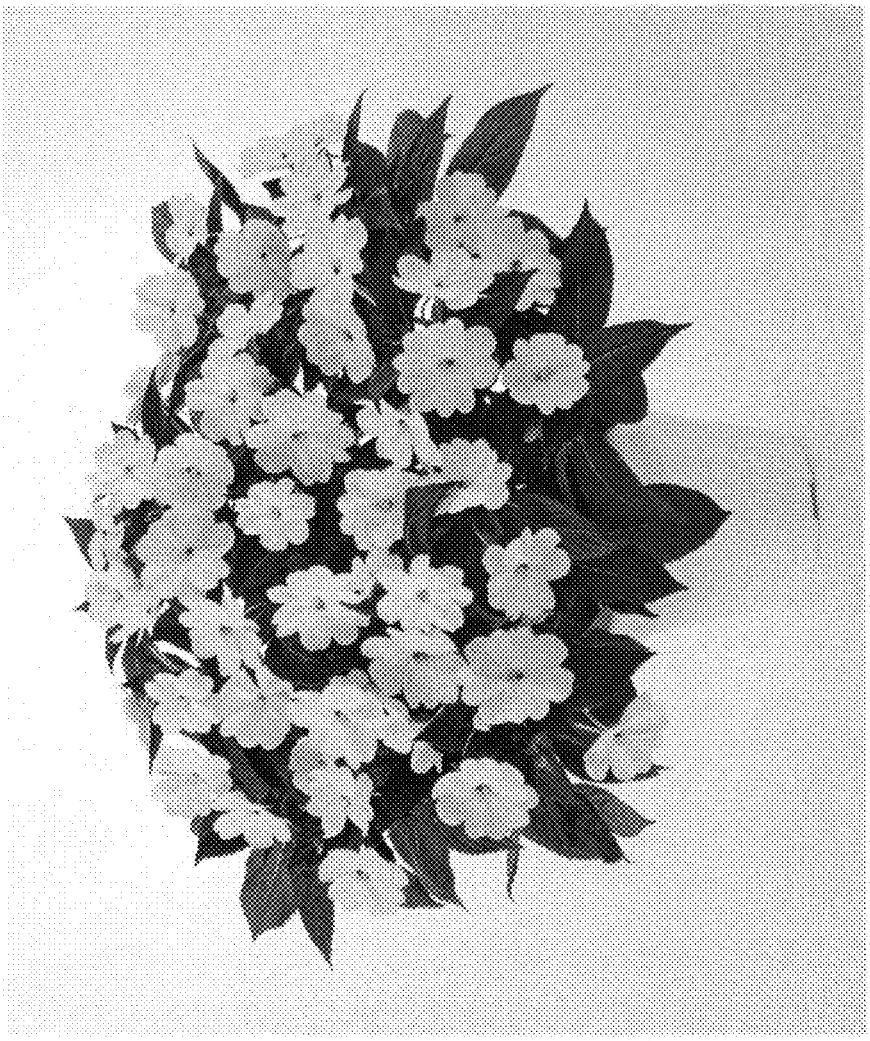

Latin name of the genus and species: *Impatiens hawkeri.*
Variety denomination: 'DHARWHITE'.

BACKGROUND OF THE INVENTION

The new *Impatiens* cultivar is the product of a planned breeding program conducted by the inventor, Gavriel Danziger, in Moshav Mishmar Hashiva, Israel. The objective of the breeding program was to produce new *Impatiens* varieties for ornamental commercial applications. The cross resulting in this new variety was made during September of 2013.

The seed parent is the, unpatented, proprietary variety referred to as *Impatiens* 'BM-2839'. The pollen parent is the unpatented, propriety variety referred to as *Impatiens* 'BM-3877'. The new variety was discovered in February of 2014 by the inventor in a group of seedlings resulting from the September 2013 crossing, in a research greenhouse in Moshav Mishmar Hashiva, Israel.

Asexual reproduction of the new. cultivar was first performed by vegetative cuttings. The cuttings are from an apical bud that has no more than two expanded leaves and three to four immature leaves present. This was first performed at a research greenhouse in Moshav Mishmar Hashiva, Israel in February of 2014 and has shown that the unique features of this cultivar are stable and reproduced true to type in multiple successive generations.

SUMMARY OF THE INVENTION

The cultivar 'DHARWHITE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DHARWHITE' These characteristics in combination distinguish 'DHARWHITE' as a new and distinct *Impatiens* cultivar:

1. Large flowers.
2. White flower color.
3. Well branched plants.
4. Good resistance to sunny conditions.

Plants of the new cultivar 'DHARWHITE' are similar to plants of the seed parent, *Impatiens* in most horticultural characteristics, however, plants of the new cultivar 'DHARWHITE' differ in the following;

1. New variety has solid green foliage while the seed parent has variegated foliage.
2. New variety has larger flowers than the parent.

Plants of the new cultivar 'DHARWHITE' are similar to plants of the pollen parent, *Impatiens* in most horticultural characteristics, however, plants of the new cultivar 'DHARWHITE' differ in the following;

1. The new variety has smaller flowers than the pollen parent.
2. The new variety is more vigorous while the parent is more compact.

COMMERCIAL COMPARISON

Plants of the new cultivar 'DHARWHITE' are comparable to the commercial variety *Impatiens* 'SAKIMP027' U.S. Plant Pat. No. 24,320. The two *Impatiens* varieties are similar in most horticultural characteristics; however, the new variety 'DHARWHITE' differs in the following:

1. Leaf size of the new variety is larger
2. Growth habit of the new variety is more vigorous, plants of this comparator are more compact.

Plants of the new cultivar 'DHARWHITE' can also be compared to the patented commercial variety *Impatiens* 'SAKIMP018', U.S. Plant Pat. No. 21,768. The two *Impatiens* varieties are similar in most horticultural characteristics; however, the new variety 'DHARWHITE' differs in the following:

1. Leaf size of the new variety is larger
2. Growth habit of the new variety is more vigorous, plants of this comparator are more compact.

3. Leaf color of the new variety is green, leaf color of the comparator is variegated yellow and green.

BRIEF DESCRIPTION OF THE PHOTOGRAPHS

The accompanying photograph in FIG. 1 illustrates in full color a typical plant of 'DHARWHITE' grown outdoors, in a 16 cm pot. Age of the plant photographed is approximately 14 weeks from a rooted cutting.

Figure 2:
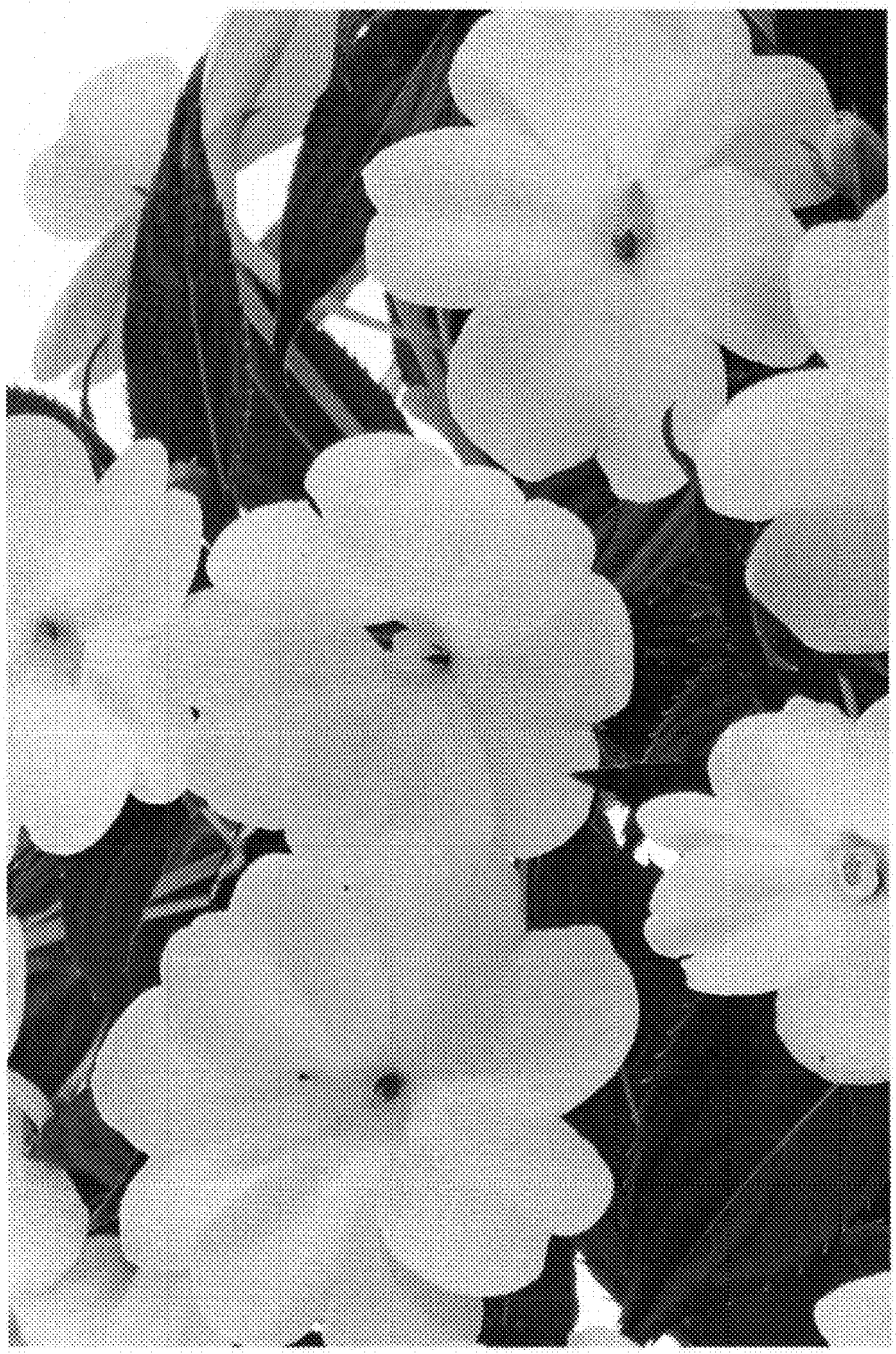

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DHARWHITE' plants grown in the Autumn, in a greenhouse, in Moshav Mishmar Hashiva, Israel. The growing temperature ranged from 20° C. to 30° C. during the day and from 15° C. to 25° C. during the night. General light conditions are bright, normal sunlight. Measurements and numerical values represent averages of typical plant types.

Botanical classification: *Impatiens hawkerii* 'DHARWHITE'.

PROPAGATION

Type of propagation typically used: Cutting.

Time to initiate roots: 10-14 days Summer, 14-20 days Winter.

Root description: Fibrous adventitious roots.

PLANT

Age of plant described: Approximately 14 weeks.

Container size of the plant described: 16 cm.

Growth habit: Mounded.

Height: Average range 30-35 cm.

Plant spread: 40 cm.

Growth rate: Vigorous.

Branching characteristics: Very well branched.

Length of primary lateral branches: 25 to 30 cm.

Quantity of primary lateral branches: 5-10.

Characteristics of primary lateral branches:

*Form*.—Oval shape.

*Diameter*.—1 cm.

*Color*.—Near RHS Yellow-Green 146B.

*Texture*.—Smooth.

*Strength*.—Strong.

*Internode length*.—5-8 cm.

FOLIAGE

Leaf:

*Quantity*.—Approximately 25-30 per branch.

*Average length*.—9 cm.

*Average width*.—4 cm.

*Shape of blade*.—Lanceolate

*Apex*.—Apiculate.

*Base*.—Acuminate.

*Margin*.—Ciliate.

*Texture of top surface*.—Smooth.

*Texture of bottom surface*.—Smooth.

*Pubescence*.—None.

*Color*.—Young foliage upper side: Near RHS Yellow-Green 146A. Young foliage under side: Near RHS Yellow-Green 147B. Mature foliage upper side: Near RHS Yellow-Green 147A. Mature foliage under side: Near RHS Yellow-Green 147B.

*Venation*.—Type: Pinnate. Venation color upper side: Near RHS Yellow-Green 144D. Venation color under side: Near RHS Yellow-Green 144D.

*Petiole*.—Length: 1.0 to 1.5 cm. Diameter: 0.5 cm. Color: Near RHS Yellow-Green 144D. Texture: Smooth.

FLOWER

Natural flowering season: Flowers at any day length. All year round in a controlled greenhouse environment. Flowering is continuous from spring until fall in an outdoor garden under conditions found in Israel.

Days to flowering from rooted cutting: 10 weeks.

Inflorescence and flower type and habit: Single flowers raised above the foliage. The corolla consists of five petals.

Rate of flower opening: 10 to 15 days from bud to fully opened flower.

Flower longevity on plant: 5-8 days.

Persistent or self-cleaning: Self-cleaning.

Bud:

*Shape*.—Ovate.

*Length*.—1.5 cm.

*Diameter*.—1.0 cm.

*Color*.—Near RHS Green-White 157C.

Flower size:

*Diameter*.—6.0 cm.

*Depth*.—Approximately 5.0 including spur.

Petals:

*Quantity*.—5.

*Arrangement*.—Overlapping.

*Length*.—3.0 cm.

*Width*.—2.5 to 3.0 cm.

*Shape*.—Obcordate.

*Apex*.—Cordate.

*Base*.—Acute.

*Margin*.—Entire.

*Texture, upper and lower surfaces*.—Smooth.

*Color*.—When opening, upper surface: Near RHS White N155D. When opening, lower surface: Near RHS White N155D. Fully opened, upper surface: Near RHS White N155D. Fully opened, lower surface: Near RHS White N155D and N155C.

Spurs:

*Quantity per flower*.—1.

*Length*.—4.5 cm.

*Diameter*.—0.2 cm.

*Aspect*.—Spur curvature 40°-45° from peduncle.

*Color*.—Towards base: Near RHS Yellow-Green 149D. Apex: Near RHS Yellow-Green 149C.

Sepals:

*Quantity*.—2.

*Length*.—2.0 cm.

*Width*.—0.8 cm.

*Shape* (*overall*).—Oblong. Apex: Caudate. Base: Rounded.

*Margin*.—Entire.

*Color*.—Near RHS Yellow-green 1445B, upper and lower surfaces.

Peduncles:

*Length*.—5.0 cm.

*Diameter*.—0.3 cm.

*Angle*.—About 45° to the lateral branch.

*Strength*.—Sturdy, flexible.

*Texture*.—Smooth.

*Color*.—Near RHS Yellow-Green 145D.

Fragrance: None.

REPRODUCTIVE ORGANS

Stamens: There are five stamens with anthers that are more or less fused and form a cap over the ovary.

*Number*.—5.

Anthers:

*Shape*.—Oblong.

*Length*.—Approximately 0.5 cm.

*Color*.—Near RHS White 155B.

*Pollen*.—Not produced.

Pistil:

*Number*.—1.

*Length*.—0.5 cm.

*Style*.—Length: 0.5 cm. Color: Near RHS Yellow-Green 144A.

*Stigma*.—Shape: Round. Color: Near RHS Yellow-Green 149D. Ovary Color: Near RHS Yellow-Green 144D.

OTHER CHARACTERISTICS

Seeds and fruits: 5-10 seeds per fruit. Minute, dust-like, brown-grey in color. Color not accurately measured with R.H.S. chart due to size.

Disease/pest resistance: Neither resistance nor susceptibility to normal diseases and pests of Impatiens have been observed.

Temperature tolerance: Tolerant to temperatures between 5° C. and 30° C. (grows best at 10° C.-28° C.).

What is claimed is:

1. A new and distinct cultivar of New Guinea *Impatiens* plant named 'DHARWHITE' as herein illustrated and described.

* * * * *